United States Patent [19]

Hader

[11] Patent Number: 5,219,286
[45] Date of Patent: Jun. 15, 1993

[54] IMPLANTABLE DENTAL SUPPORT STRUCTURE

[75] Inventor: Helmut Hader, Auvernier, Switzerland

[73] Assignee: Firma H. Hader Dental Products SA, La Chaux-de-Fonds, Switzerland

[21] Appl. No.: 952,436

[22] Filed: Sep. 28, 1992

[30] Foreign Application Priority Data

Sep. 27, 1991 [CH] Switzerland ............... 2875/91
Apr. 3, 1992 [CH] Switzerland ............... 1089/92

[51] Int. Cl.⁵ .................. A61C 13/12; A61C 13/225
[52] U.S. Cl. ............................................. 433/172
[58] Field of Search ............... 433/167, 172, 173, 174, 433/176

[56] References Cited

U.S. PATENT DOCUMENTS 3,748,739  7/1973  Thibert .
4,072,119 12/1977  Linkow et al. .
4,907,969  3/1990  Ward ............................ 433/173
4,931,016  6/1990  Sillard ........................ 433/167 X
5,052,928 10/1991  Andersson ..................... 433/172

FOREIGN PATENT DOCUMENTS 0393324 10/1989 European Pat. Off. .

Primary Examiner—Gene Mancene
Assistant Examiner—Nicholas D. Lucchesi
Attorney, Agent, or Firm—Herbert Dubno; Andrew Wilford

[57] ABSTRACT

An implantable dental support structure has a plurality of identical posts each having an end forming a seat and each formed with a bore opening at the seat and respective female elements each having a ball head shaped to fit in the post seat, internally formed with a ball cavity, traversed by a main bore, formed with a laterally open side bore, and also having a stem projecting from the head in general alignment with the side bore but opposite thereto and formed with a socket open away from the head. Respective male elements each have a ball head shaped to fit complementarily in a respective one of the female element cavities and formed with a throughgoing bore alignable with the main bore of the respective female element, and also have a bar projecting from the respective ball head out of the respective cavity through the respective side bore and into the socket of an adjacent female element stem. Respective screws on each post each project through the main bores of the respective female and male element ball heads and are seated in the respective post bore.

13 Claims, 3 Drawing Sheets

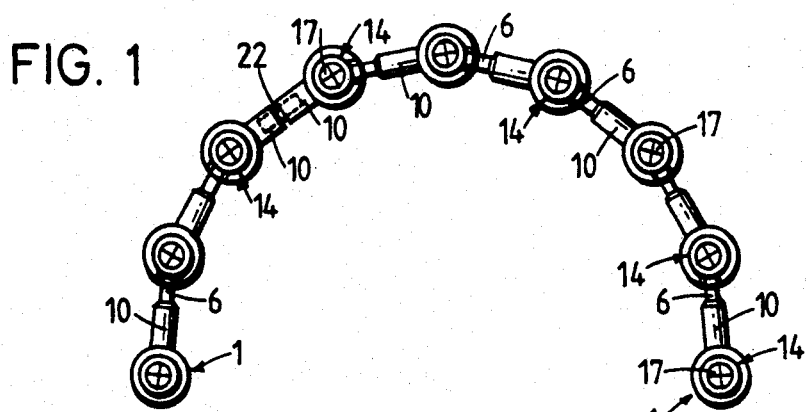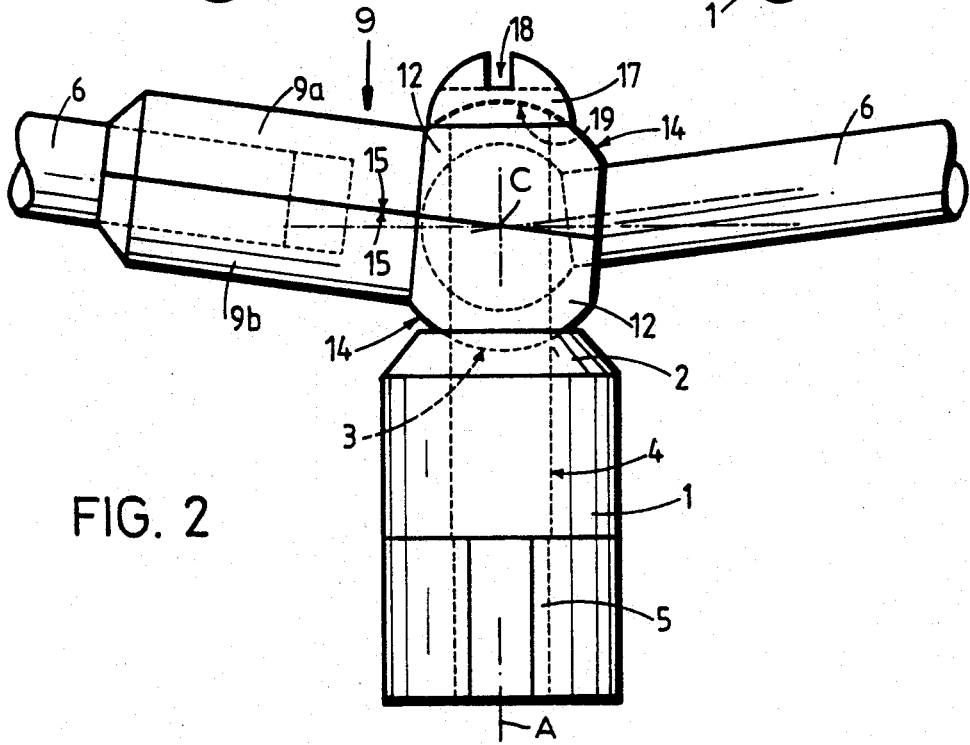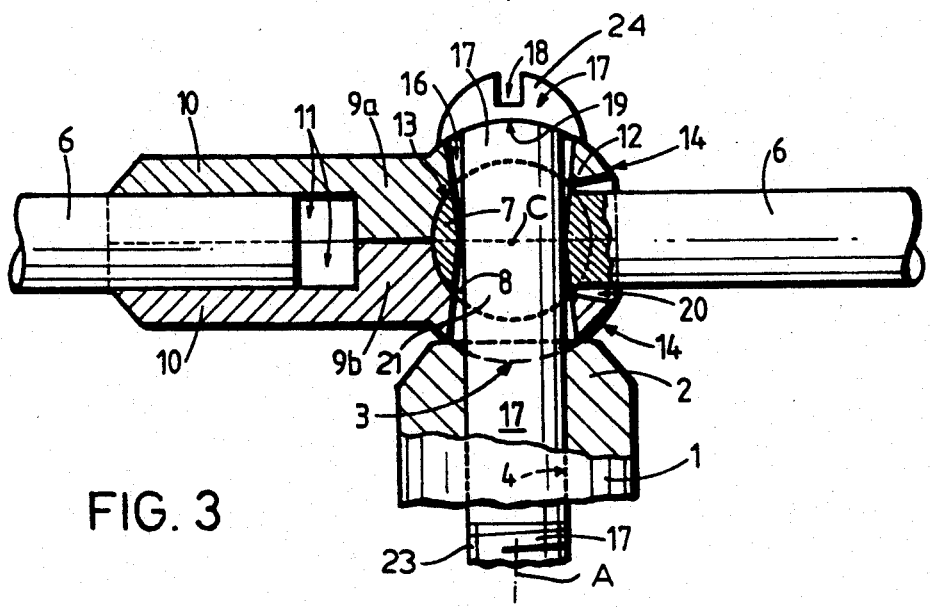

IMPLANTABLE DENTAL SUPPORT STRUCTURE

FIELD OF THE INVENTION

The present invention relates to a dental implant support structure. More particularly this invention concerns a device which is implanted in the mandible to serve as a support for a dental prosthesis.

BACKGROUND OF THE INVENTION

In order to avoid bone resorption it has become standard practice to mount a major dental prosthesis, for instance a full plate, on a structure that itself is carried on implants set right in the patient's bone structure and projecting up through the gingival tissues. Thus the patient's actual mandible carries the prosthesis in a manner akin to the anchoring of the patient's one-time own teeth in his or her jaw.

Such a standard structure has several anchors that are surgically implanted in the mandible. Typically three anchor locations are employed, one at each ramus bone and one at the symphysis, that project up through the gingival tissue and are joined by bars which extend generally parallel to the occlusal plane and to which is clipped the dental prosthesis.

In European patent document 393,324 based on a German priority of 10 Apr. 1989 the anchors are constituted as posts having at their upper ends small seats in which small ball heads of connecting bars can be clamped. Such an arrangement is not very strong, the posts must be exactly positioned, and the bars are fairly complex telescoping structures that require that the posts be relatively widely spaced. Furthermore the offset mounting of the ends of two bar ends on a single post makes it difficult to conform the structure to a tightly curved arch.

In U.S. Pat. No. 3,748,739 of Thilbert four implanted anchors are joined by complicated articulated bars. More than four anchor locations is impossible due to the complexity of the coupling bars so that resorption of bone between the anchors is a problem.

Another system is described in U.S. Pat. No. 4,062,119 of Linkow. It uses three anchor points that are joined by a massive structure. Substantial surgery is needed to seat each of the anchors, but the intermediate bone is subject to resorption. Furthermore the three anchors must be accurately positioned for the structure to fit properly.

OBJECTS OF THE INVENTION

It is therefore an object of the present invention to provide an improved implantable support structure for a dental prosthesis.

Another object is the provision of such an improved implantable support structure for a dental prosthesis which overcomes the above-given disadvantages, that is which can be implanted with minimal surgical trauma, which can use a large number of bone anchor points, and which can readily adapt to irregular positioning of the actual anchors.

SUMMARY OF THE INVENTION

An implantable dental support structure has according to the invention a plurality of identical posts each having an end forming a seat and each formed with a bore opening at the seat and respective female elements each having a ball head shaped to fit in the post seat, internally formed with a ball cavity, traversed by a main bore, formed with a laterally open side bore, and also having a stem projecting from the head in general alignment with the side bore but opposite thereto and formed with a socket open away from the head. Respective male elements each have a ball head shaped to fit complementarily in a respective one of the female-element cavities and formed with a throughgoing bore alignable with the main bore of the respective female element, and also have a bar projecting from the respective ball head out of the respective cavity through the respective side bore and into the socket of an adjacent female-element stem. Respective screws on each post each project through the main bores of the respective female- and male-element ball heads and are seated in the respective post bore.

This system therefore allows the posts to be placed without any particular pains as to their relative spacings and whether or not they are parallel to each other so that they can be sited where the patient's anatomy permits. Once the posts are in they are joined together by the male and female elements which can extend at substantial angles to each other and to the posts, and these elements telescope in each other so that they can compensate for quite some variation in spacing between adjacent posts. The screws actually traverse bores in both the male and female elements and compress both of the concentric heads against the seat at the top of the respective post to make an extremely robust assembly. It is even possible to partially disassemble the support structure, if necessary, for subsequent replacement or repair of the male or female coupling elements. The denture is typically provided with clips that engage over the stems of the female elements.

According to the invention the assembly also comprises a single bar coupling of uniform shape and cross section and having opposite ends each received in a respective socket of a respective female element.

In accordance with a further feature of the invention each female element is formed by a pair of substantially identical halves each forming half of the respective stem and ball head and joined at a generally planar surface with the respective female-element main bore generally perpendicular to the generally planar surface. With such an arrangement the screw will hold the halves together in the finished assembly. Alternately each female element is formed by a pair of parts joined at a surface generally bisecting the respective main bore and head cavity. In the latter case the two parts are welded together after a male-element ball head is positioned in the cavity.

The bores of the female elements according to the invention flare frustoconically outward. In addition the main bore of each male-element ball head has a minimum diameter central region and flares outwardly in both directions therefrom. This minimum-diameter central region is of the same diameter as the outside of the shaft of the screw.

The female-element cavities according to the invention are substantially spherical and of predetermined diameter and the male-element ball heads are also substantially spherical and of substantially the same predetermined diameter. Furthermore the post seats are part spherical and of substantially the same radius of curvature as the female-element heads. The screws each have a threaded shaft engaged in the respective post bore and a head having a surface bearing on and shaped complementary to the respective female-element head.

Each bar of this invention is of cylindrical shape and has a predetermined outside diameter and each female-element stem socket is of complementary cylindrical shape. Each female-element side bore can be exactly aligned with the respective stem or centered on an axis extending at a large obtuse angle to a center axis of the respective stem.

BRIEF DESCRIPTION OF THE DRAWING

The above and other objects, features, and advantages will become more readily apparent from the following, reference being made to the accompanying drawing in which:

FIG. 1 is a top view of an implant structure according to the invention;

FIG. 2 is a large-scale side view of a detail of the implant structure;

FIG. 3 is a view like FIG. 2 but partly in section;

SPECIFIC DESCRIPTION

Figure 4:
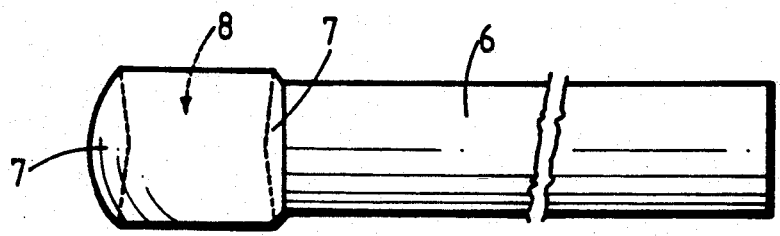
FIGS. 4 and 5 are side views of the male and female elements of the structure.
Figure 5:
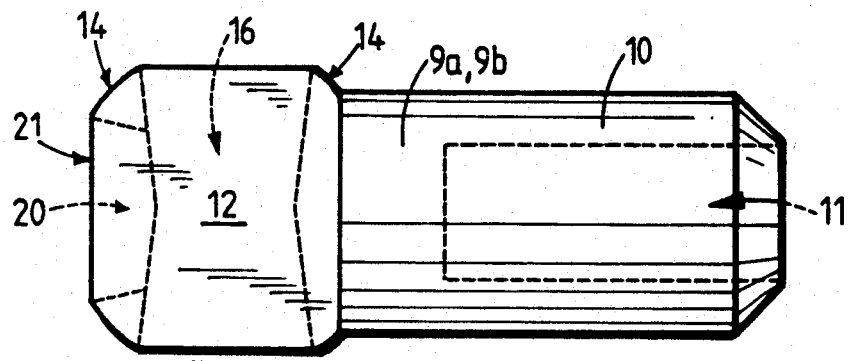
Figure 6:
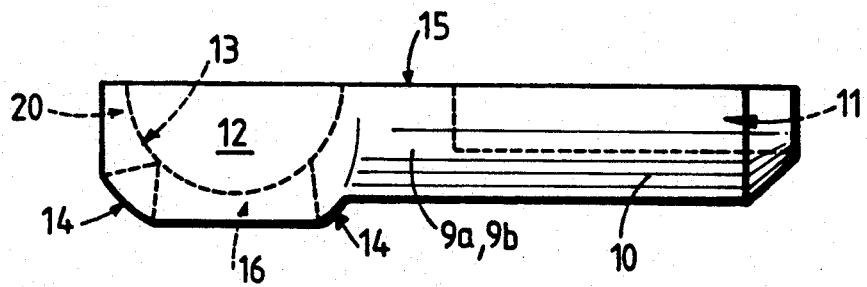
FIG. 6 is a side view of a female-element half of the structure.
Figure 7:
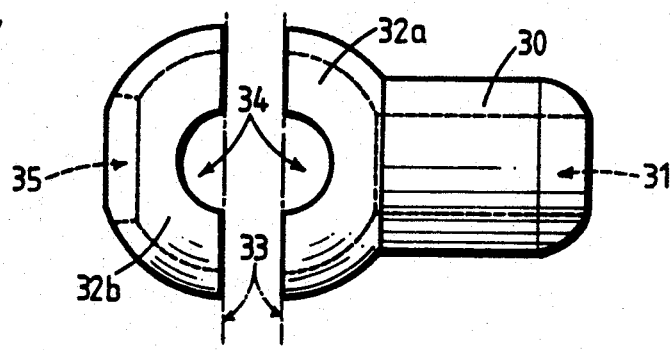
FIGS. 7 and 8 are top and side views of another female element prior to assembly.
Figure 8:
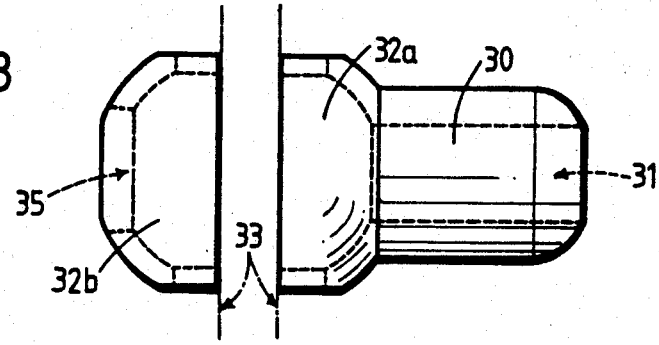
Figure 9:
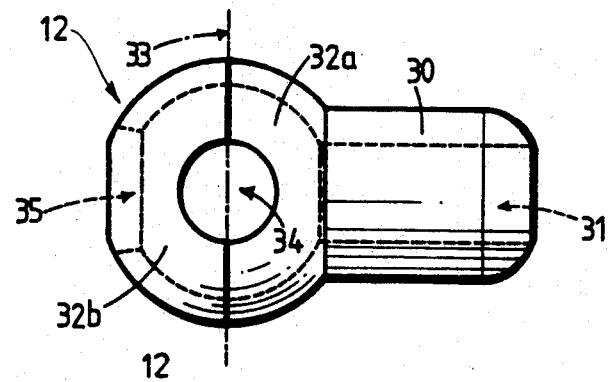
FIG. 9 is a top view of the other female element after assembly.

As seen in FIG. 1 a dental implant structure according to the invention basically comprises a plurality, here nine, of identical posts 1, an equal number of identical male elements or bars 6, an equal number of identical two-part female elements or sockets 9, an equal number of screws 17, and a single male coupling bar 22, all made of a biologically compatible metal. The system is therefore comprised of five different parts.

Each post 1 as seen in FIGS. 1 and 2 is adapted to be seated in an anchor itself mounted in the patient's mandible, either seated directly in the mandible or screwed into a tooth root or socket, and is centered on a normally upright axis A. It has a frustoconically tapered upper end 2 and a vertically axially open part-spherical seat 3, both centered on the axis A. In addition the posts 1 are each formed along the respective axis A with a central bore 4 having a lower threaded region 5.

Each female socket element 9 is comprised of two identical parts 9a and 9b joined together along a plane 15 and having laterally projecting stems 10 that together define a laterally open blind bore or socket 11 of cylindrical shape. Furthermore each part 9 has a mainly spherical head 12 having an outer surface 14 of a radius of curvature the same as the seat 3 and normally sitting inside this seat 3. Furthermore each head 12 is concentrically formed with an internal spherical cavity 13 and, relative to a center C normally lying on the axis A, with a radially open and radially outwardly frustoconically flared aperture 20 in line with the socket 11. The interior of the socket 11 may be formed with longitudinal ridges. Furthermore the head 12 is formed with a diametrically throughgoing double-flared passage 16 centered on an axis perpendicular to the plane 15.

As seen in FIG. 4, each male bar 6 is basically cylindrical and is formed with a spherical head 7 in turn formed with a diametrically throughgoing double-flared bore 8 whose central waist region of minimum diameter has a diameter equal to that of the bore 4 above the thread 5. The radius of curvature of the outside surface of the head 7 is identical to the radius of curvature of the inside of the cavity 13 of the socket element 9. The outside diameter of the bar 6 is identical to the inside diameter of the socket 11 of the female part 9.

The screw 17 has a cylindrical shaft 21 of an outside diameter equal to the minimum diameter of the waisted central region of the 8 and a head 24 with a semispherically concave lower surface 19 of the same radius of curvature as the outside of the ball head 12. The top of the screw head 24 is formed with one or two slots 18 and the lower end of the shaft with a screwthread 23 complementary to the screwthread 5.

The structure is made by first seating the posts 1 in the patient's jaw by means of conventional implant anchors and adhesive. There is no need to set them at an exact spacing and in fact they need not even be perfectly parallel to each other.

The illustrated assembly is then normally assembled piecemeal, starting with a female-element half 9b set in a seat 3, then with a male bar 6 fitted to the half cavity 11, the other identical female-element half 9a fitted over it, and the two parts 9a and 9b traversed by and secured in place by a screw 17. On the rearmost teeth no ball 7 is in the female-element cavity 13, but in all the others there is such a ball 7. Instead of a headed bar 6 a plane cylindrical bar 22 is used between two of the female elements 9 as shown in the upper left in FIG. 1 to close the arc. Once everything is in place the screws 17 are all tightened to secure the elements 6 and 9 solidly in place on the posts 1.

Due to the flared shape of the holes 20 and 16 some angular misalignment can easily be tolerated. In addition the simple shapes of the elements lets the posts 1 be mounted relatively close together, giving multipoint support for the prosthesis that eventually is clipped to the structure so that bone resorption is avoided and considerable stress can be withstood by the assembly. Also, the patient's gums do not need to be laid open completely, but only cut where the posts 1 are to pass, minimizing trauma.

FIGS. 7 through 10 show another system where a female element has a one-piece cylindrically tubular stem 30 forming a bar-receiving socket hole 31 and carrying a semispherical head half or shell 32a adapted to be joined to another shell head half 32b along a join line 33. When joined, typically by laser welding, the two halves 32a and 32b form a diametrally throughgoing hole 34 like the hole 16 and a lateral hole 35 like the hole 20. The half 32b is fitted over a bar 6 so its head 7 is in the cavity between the halves 32a and 32b before same are welded together. Here the socket 31 opens into the head cavity so that if cement is put in this socket 31 it will fill the head cavity around the bar head 7, which would have a grooved surface, to further insure a solid anchoring.

Figure 10:
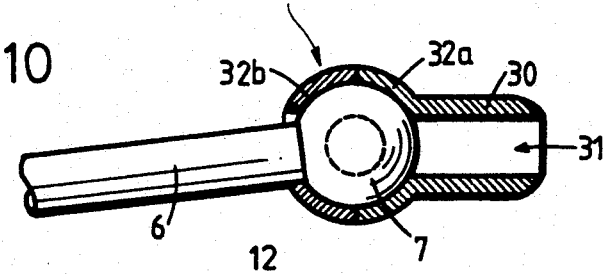
FIGS. 10 and 11 are top views partly in section illustrating further arrangements according to the invention.
Figure 11:
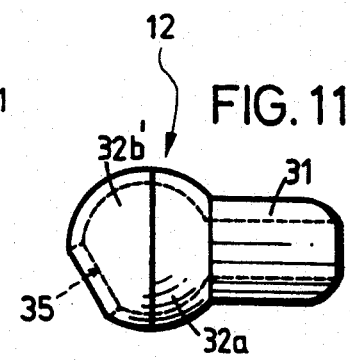
Figure 12:
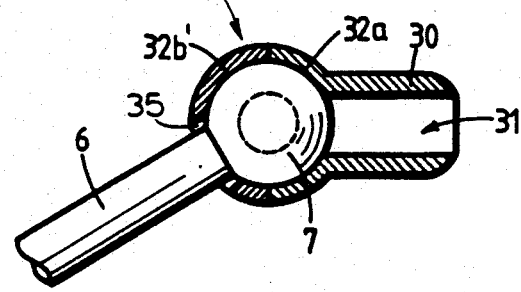
FIG. 12 is a top view of the female element of the arrangement of FIG. 11.

FIGS. 10 and 11 show a head half 32b' whose hole 35 is not axially aligned with the stem 31 so that extreme angular offsets can be tolerated. Such an arrangement is useful at the canine-tooth region of the dental arch or for a very small jaw.

I claim:

1. An implantable dental support structure comprising:

a plurality of identical posts each having an end forming a seat and each formed with a bore opening at the seat;

respective female elements each having a ball head shaped to fit in a respective post seat, internally formed with a ball cavity, traversed by a main bore, and formed with a laterally open side bore, both bores opening into the cavity, and a stem projecting from the head in general alignment with the side bore but opposite thereto and formed with a socket opening away from the head;

respective male elements each having a ball head fitted complementarily in the cavity of a respective one of the female elements and formed with a throughgoing bore alignable with the main bore of the respective female element, and a bar projecting from the ball head out of the respective cavity through its respective side bore and into the socket of an adjacent female element stem; and a respective screw on each post each projecting through the main bores of the respective female and male-element ball heads and seated in a respective one of the post bores.

2. The structure defined in claim 1, further comprising a single bar coupling of uniform shape and cross section and having opposite ends each received in a respective socket of a respective female element.

3. The structure defined in claim 1 wherein each female element is formed by a pair of substantially identical halves each forming half of the respective stem and ball head and joined at a generally planar surface with the respective female element main bore generally perpendicular to the generally planar surface.

4. The structure defined in claim 1 wherein the bores of the female elements flare frustoconically outward.

5. The structure defined in claim 1 wherein the throughgoing bore of each male element ball head has a minimum diameter central region and flares outwardly in both directions therefrom.

6. The structure defined in claim 1 wherein female element ball cavities are substantially spherical and of predetermined diameter and the male element ball heads are also substantially spherical and of substantially the same predetermined diameter as the female element ball cavities.

7. The structure defined in claim 1 wherein the post seats are part spherical and of substantially the same radius of curvature as the female element heads.

8. The structure defined in claim 1 wherein the screws each have a threaded shaft engaged in its respective post bore and a head having a surface bearing on and shaped complementary to its respective female element head.

9. The structure defined in claim 1 wherein each bar is of cylindrical shape and has a predetermined outside diameter and each female element stem socket is of complementary cylindrical shape.

10. The structure defined in claim 1 wherein each female element is formed by a pair of parts joined at a surface generally bisecting its respective main bore and head cavity.

11. The structure defined in claim 1 wherein each female element side bore is exactly aligned with its respective stem.

12. The structure defined in claim 1 wherein each female element side bore is centered on an axis extending at a large obtuse angle to a center axis of its respective stem.

13. An implantable dental support structure comprising:

plurality of identical posts each having an end forming a semispherical seat of predetermined large diameter and each formed with a threaded bore opening at its respective seat;

respective female elements each having,, a ball head shaped to fit in a respective post seat and of an outside diameter equal to the large diameter, internally formed with a substantially spherical ball cavity of predetermined small diameter, traversed diametrically by a main bore, and formed with a laterally open side bore opening into the cavity, and a stem projecting from the head in general alignment with the side bore but opposite thereto and formed with a cylindrical socket opening away from the head;

respective male elements each having a ball head of the predetermined small diameter and fitting complementarily in the cavity of respective one of the female elements cavities and formed with a throughgoing bore alignable with the main bore of the respective female element, and a cylindrical bar projecting from the ball head out of the respective cavity through the respective side bore and fitting complementarily into the socket of an adjacent female element stem; and a respective screw on each post projecting through the main bores of the respective female and male element ball heads and seated in a respective post bore.

* * * * *